Figure 1:
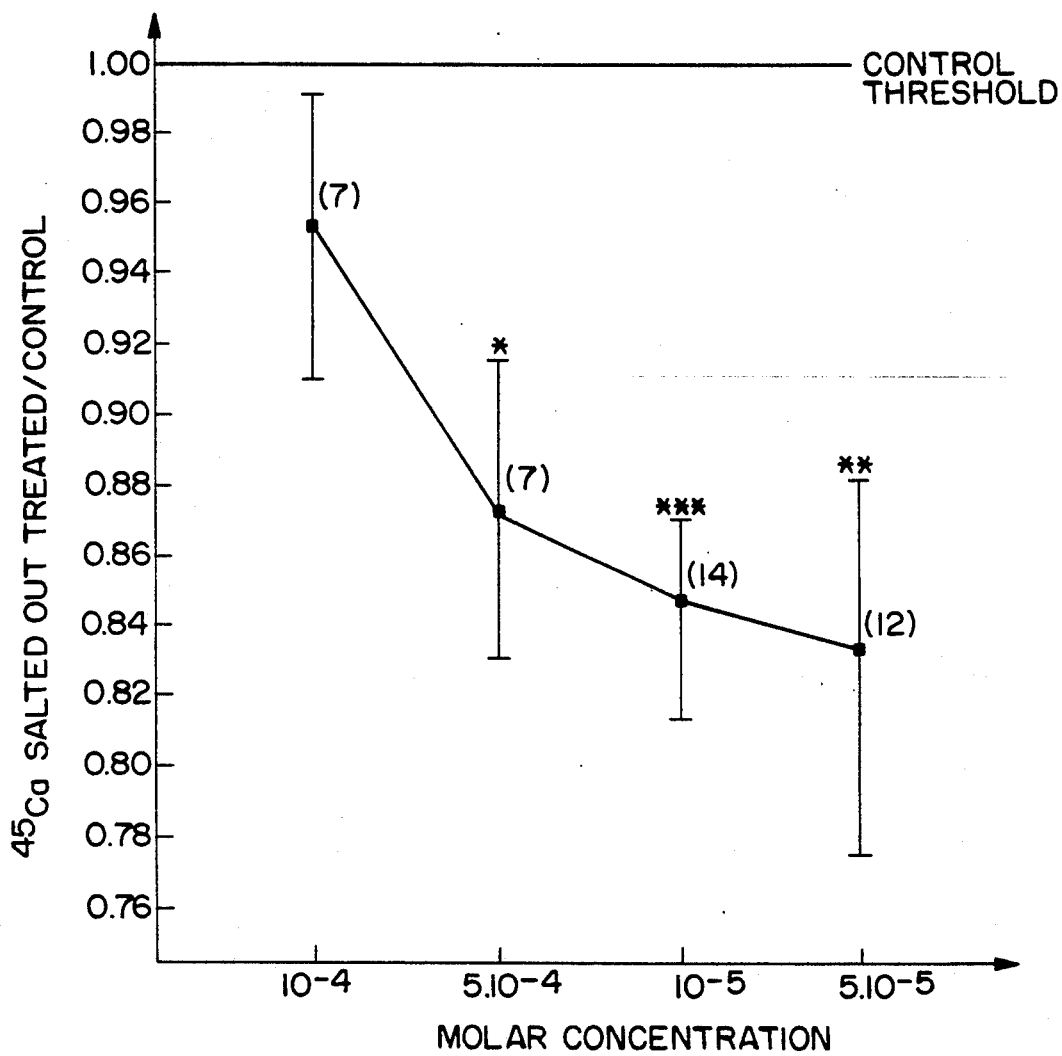

United States Patent

Wierzbicki et al.

[11] Patent Number: 5,175,294
[45] Date of Patent: Dec. 29, 1992

[54] NEW THIOPHENE COMPOUNDS AS INTERMEDIATES

[75] Inventors: Michel Wierzbicki, L'Etang la Ville; Frédéric Sauveur, Argenteuil; Jacqueline Bonnet, Paris; Martine Brisset, Caen; Charles Tordjman, Boulogne, all of France

[73] Assignee: Adir et Compagnie, Courbevoie, France

[21] Appl. No.: 740,075

[22] Filed: Aug. 5, 1991

Related U.S. Application Data

[62] Division of Ser. No. 617,501, Nov. 23, 1990, Pat. No. 5,061,704.

[30] Foreign Application Priority Data

Nov. 24, 1989 [FR] France ............... 89 15458

[51] Int. Cl.⁵ ............... C07D 409/06; C07D 413/06
[52] U.S. Cl. ............... 544/379; 544/146; 546/213; 548/527; 549/77
[58] Field of Search ............... 549/77; 544/146, 379; 546/213; 548/527

[56] References Cited

U.S. PATENT DOCUMENTS 4,705,802 11/1987 Lautenschläger et al. ............ 549/74
4,874,876 10/1989 O'Reilly et al. ............ 549/74
5,061,704 10/1991 Wierzbicki et al. ............ 544/379

FOREIGN PATENT DOCUMENTS 2453172 12/1980 France ............... 544/379

Primary Examiner—Mukund J. Shah
Assistant Examiner—F. Bernhardt
Attorney, Agent, or Firm—Gordon W. Hueschen

[57] ABSTRACT

New thiophene compounds of the formula:

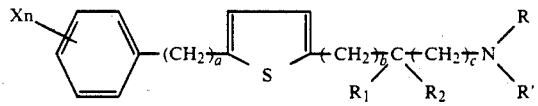

in which:
X represents hydrogen, halogen, $C_1$–$C_5$alkyl or alkoxy or dialkylamino;
n represents 1 or 2;
a represents an integer of from 2 to 6;
b represents 2 or 3;
c represents 1 or 2, and is such that b+c=4;
$R_1$ and $R_2$ represent hydrogen or ($C_1$–$C_5$)alkyl, or together with the carbon atom to which they are bonded form a hydrocarbon ring containing from 3 to 6 carbon atoms; and
R and R' represent hydrogen or ($C_1$–$C_5$)alkyl, or together with the nitrogen atom to which they are bonded form a pentagonal or hexagonal heterocycle optionally containing an oxygen atom or a second nitrogen atom which may itself be substituted; and their physiologically tolerable salts.

The products of the invention can be used therapeutically especially in the treatment of pathologies that are characterized by a loss of bone tissue.

As new intermediate products used in the synthesis of the compounds I above defined, the amides of the formula:

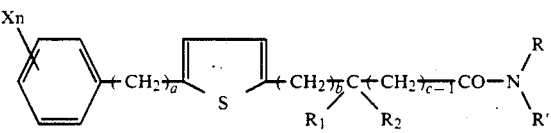

in which: X, n, a, b, c, $R_1$, $R_2$, R and R' are as above defined.

8 Claims, 1 Drawing Sheet

NEW THIOPHENE COMPOUNDS AS INTERMEDIATES

The present application is a division of our prior-filed copending application Ser. No. 07/617,501, filed Nov. 23, 1990, now U.S. Pat. No. 5,061,704, issued Oct. 29, 1991.

The present invention provides new thiophene compounds of the general formula I:

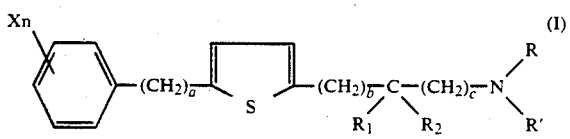

in which:
- X is selected from the group consisting of: a hydrogen atom, halogen atoms, straight-chain and branched alkyl and alkoxy radicals each having from 1 to 5 carbon atoms, and dialkylamino radicals in which each alkyl group contains from 1 to 5 carbon atoms;
- n is selected from the group consisting of: 1 and 2;
- a is selected from the group consisting of: integers of from 2 to 6 inclusive;
- b is selected from the group consisting of: 2 and 3;
- c is selected from the group consisting of: 1 and 2, and is such that $b+c=4$; $R_1$ and $R_2$, which may be the same or different, are each selected from the group consisting of: a hydrogen atom and alkyl radicals having from 1 to 5 carbon atoms, and
- $R_1$ and $R_2$ together with the carbon atom to which they are bonded form a hydrocarbon ring containing from 3 to 6 carbon atoms inclusive; and
- R and R', which may be the same or different, are each selected from the group consisting of: a hydrogen atom and alkyl radicals having from 1 to 5 carbon atoms, and
- R and R' together with the nitrogen atom to which the are bonded form a heterocyclic radical selected from the group consisting of pentagonal and hexagonal heterocyclic radicals each containing one nitrogen atom, one nitrogen atom and one oxygen atom, and two nitrogen atoms, and each of these heterocyclic radicals substituted by a substituant selected from the group consisting of: straight-chain and branched alkyl radicals containing 1 to 5 carbon atoms inclusive and arylalkyl, haloarylkyl, ($C_1$-$C_5$)alkyl-arylalkyl and ($C_1$-$C_5$)alkoxy-arylakyl radicals, in which the alkyl moiety of each aryl-alkyl radical has from 1 to 5 carbon atoms inclusive.

The prior art closest to the present invention is illustrated especially by:

Patent DE.3,407,510, which relates, inter alia, to the acid of the formula:

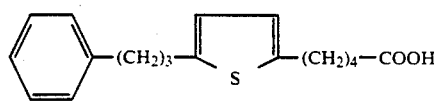

which has an anti-inflammatory activity;

F. F. KNAPP & coll., Journal of Nuclear Medicine, 27 (4), 521-531 (1986), which describes in particular the esters of formula:

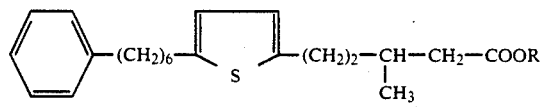

and M. M. GOODMANN & coll., J. Med. Chem. 27, 390-397 (1984) which describes, inter alia, the derivative of formula:

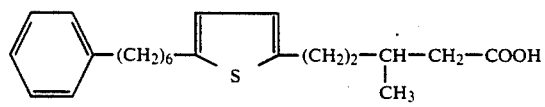

None of these reference either describes or suggests the amines of the general formula I forming the subject of the present invention, which possess an anti-resorbent bone activity which is not mentioned at all for the structurally closest acids and esters of the prior art.

The present invention also relates to a process for the preparation of the compounds of the general formula I, characterized in that:

an acid of the general formula II:

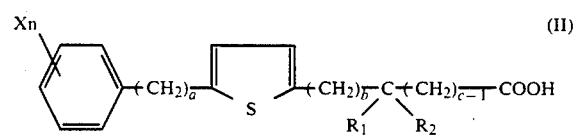

in which X, n, a, b, c, $R_1$ and $R_2$ are as defined hereinbefore is converted by means of, for example, thionyl chloride, into the corresponding acid chloride of the general formula III:

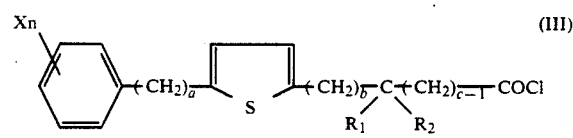

in which X, n, a, b, c, $R_1$ and $R_2$ are as defined hereinbefore, which acid chloride is used to acylate an amine of the general formula IV:

in which R and R' are as defined hereinbefore, and the amide so-obtained of the general formula V:

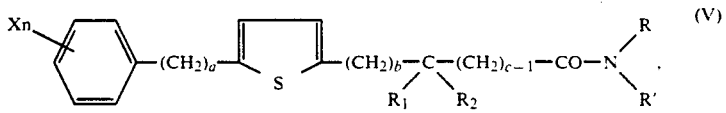

in which X, n, a, b, c, $R_1$, $R_2$, R and R' are as defined hereinbefore, is reduced.

It is especially advantageous to carry out this reduction by means of $LiAlH_4$ under reflux in a suitable solvent such as, for example, ether.

The acid of the general formula II used as starting material was prepared either from an acid of the general formula:

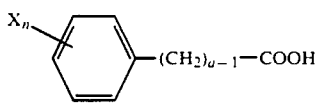

converted into the corresponding acid chloride of the general formula

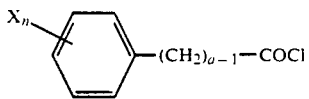

which, together with an equimolar amount of thiophene, is subjected to a Friedel-Crafts reaction in the presence of $AlCl_3$ or $SnCl_4$ to yield the compound of the general formula A:

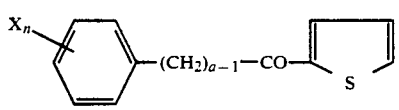

which, subjected to Wolff-Kishner reduction in the presence of potassium and hydrazine, yields a compound of the general formula B:

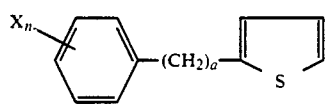

which, subjected to a Friedel-Crafts reaction with a substituted glutaric anhydride of the general formula:

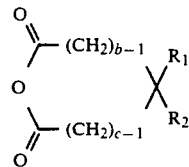

yields a compound of the general formula C:

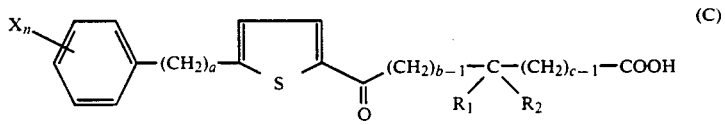

which, by means of Wolff-Kishner reduction, yields an acid of the general formula II;

or from thiophene and a substituted glutaric anhydride of the general formula:

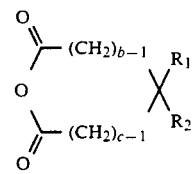

which is subjected to a Friedel-Crafts reaction in the presence of $AlCl_3$ in nitrobenzene to yield a compound of the general formula D:

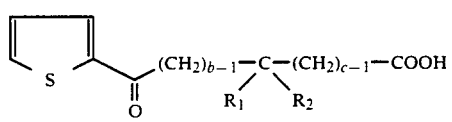

which is reduced according to the Wolff-Kishner method by means of hydrazine and potassium hydroxide to yield an acid of the general formula E:

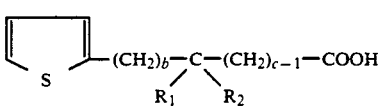

which is esterified by $CH_3OH$/para-toluenesulphonic acid to yield an ester of the general formula F:

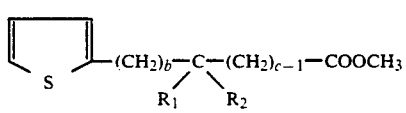

which is subjected to Friedel-Crafts acylation with $SnCl_4$ and $CH_2Cl_2$ to yield an ester of the general formula G:

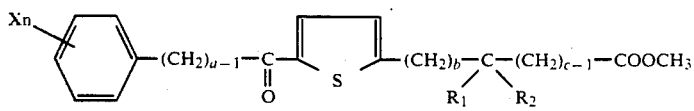

which, by means of Wolff-Kishner reduction using hydrazine and potassium hydroxide, yields an acid of the general formula II;

the variables X, N, a, b, c, $R_1$, $R_2$, R and R' in each of the above formulae having the meanings given hereinbefore.

The compounds of the general formula I yield salts with physiologically tolerable acids, which salts, as such, are included within the present invention.

The amides of the general formula V, intermediate products in the synthesis of compounds of the general formula I, are new products, which are, as such, included within the present invention.

The compounds of the present invention have valuable pharmacological and therapeutic properties especially on bone metabolism.

In a bone hyperresorption test, with retinoic acid, carried out on cultured mice, calvaria in accordance with a method inspired by J. J. REYNOLDS & coll.- Calc. Tiss. Res. 4, 339-349, (1970)-the compounds of the present invention exhibited an antiresorbent activity of from 5 to 20% at molar concentrations of from $10^{-6}$ to $5.10^{-5}$.

For example, in this test the compound forming the subject of Example 8 exhibited the activity expressed by the graph of FIG. 1 wherein each value on the ordinate is the mean value ±S. D. (the number of calvaria treated being indicated in brackets). Comparison with the control mean value *P<0.05, P<0.01, *P<0.001.

Moreover, certain compounds of the present invention, and especially the compound forming the subject of Example 9, exerted a stimulating activity on bone formation in vivo (incorporation of $^3$H-proline in the bone tissue of mice calvaria, cultured according to the method described by M. C. MEIKLE & coll. - Calcif. Tissue Int. 34, 359-364, (1982) - at concentrations of $10^{-6}$ to $10^{-5}$M).

These compounds exhibited those valuable properties on bone metabolism yet still retained an inhibitory activity on release of lipoxygenase-dependent metabolites of arachidoic acid with IC$_{50}$ values of from $10^{-6}$ to $10^{-5}$M (method of studying the biosynthesis of metabolites of arachidoic acid by polynucleates in rats stimulated by ionophore A 23187; measured by HPLC with radioactive detection).

On the other hand, these compounds are not toxic on acute oral administration to mice (LD$_{50}$≧1000 mg/kg).

As a result, the phamacological properties and the absence of toxicity of the compounds of the present invention permit their use in pathologies characterized by a loss of bone tissue, such as osteoporosis, Paget's disease, periodontitis and rheumatoid polyarthritis.

The present invention also relates to pharmaceutical compositions containing as active ingredient a compound of the general formula I or a physiologically tolerable salt thereof, in admixture or association with an appropriate pharmaceutical excipient, such as, for example, glucose, lactose, starch, talc, ethyl cellulose, magnesium stearate or cocoa butter.

The pharmaceutical compositions so-obtained are generally in dosage form and may be, for example, in the form of tablets, dragees, gelatin-coated pills, suppositories, injectable or drinkable solutions and, depending on the cases in question, may be administered orally, rectally or parenterally.

The following Examples illustrate the present invention.

I) Synthesis of the starting materials of the general formula II:

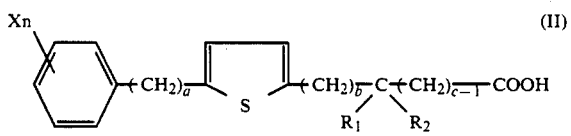

A) First method:

a) Preparation of compounds of the general formula A:

150.18 g (1 mol) of hydrocinnamic acid are added in portions to 95 ml (1.3 mol) of thionyl chloride in the cold while stirring. The reaction mixture is stirred for one hour and then heated to 40° C. until the evolution of gas has ceased. Excess thionyl chloride is distilled off under reduced pressure.

The acid chloride so-obtained and 82.55 g (1.1 mol) of thiophene are dissolved in 1.2 l of anhydrous dichloromethane. The temperature is adjusted to 0° C., with brine. 312.6 g (1.2 mol) of tin chloride are added, drop by drop, while stirring vigorously and maintaining the temperature at 0° C. After one hour at 0° C., the reaction mixture is stirred for 12 hours at room temperature, hydrolysed with 600 ml of 6 N HCl solution and decanted, and the aqueous phase is extracted 4 times with 100 ml of dichloromethane each time. The organic phases are filtered through celite, washed with an N HCl solution, an N NaOH solution and with water, then dried over magnesium sulphate and decolourised with animal black. After the solvent has been distilled off 216 g of crude oil remain.

This crude product can be distilled to yield 2-(3-phenylpropionyl)-thiophene, b.p./$10^{-2}$ torr = 135° C.

The products listed in the following Table 1 were also prepared in this manner.

TABLE 1 compounds of formula

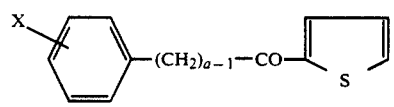

| a | X |
|---|---|
| 2 | H |
| 2 | p.CH$_3$ |
| 3 | H |
| 3 | m.F |
| 3 | p. Cl |
| 3 | m. CH$_3$ |
| 3 | p.CH$_3$ |
| 3 | p. OCH$_3$ |
| 4 | H |
| 4 | p. CH$_3$ |

TABLE 1-continued compounds of formula

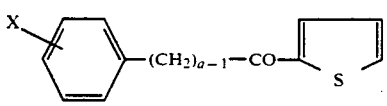

| a | X |
|---|---|
| 6 | H | b) Preparation of compounds of the general formula B:

90 g (0.416 mol) of 2-(3-phenylpropionyl)-thiophene are introduced into 500 ml of triethylene glycol. Dissolution is effected by heating to 70° C. with stirring. 62 g (1.56 mol) of hydrazine hydrate (80%) are added in one batch and the temperature is increased to 100° C. 75 g (1.335 mol) of potassium hydroxide are then rapidly added and refluxing is maintained for 45 minutes.

The water that has formed is distilled off until the temperature reaches 210°–220° C. Refluxing is thus maintained for 2 hours then the temperature of the reaction mixture is adjusted to 40° C. The mixture is hydrolysed with 400 ml of water and 100 ml of concentrated HCl, then extracted in succession with 250 ml of ether then three times with 80 ml of ether each time. The organic phase is washed in succession with a normal solution of HCl, water, a saturated aqueous solution of sodium bicarbonate, then water and is finally dried over MgSO$_4$ and decolourised with animal black. The solvent is distilled off leaving 70 g of 2-(3-phenylpropyl)-thiophene in the form of a crude oil.

The products listed in the following Table 2 were also prepared in this manner.

TABLE 2 compounds of the formula

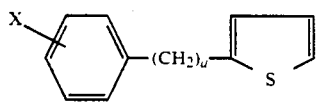

| a | X |
|---|---|
| 2 | H |
| 2 | p.CH$_3$ |
| 3 | H |
| 3 | m.F |
| 3 | p. Cl |
| 3 | m. CH$_3$ |
| 3 | p.CH$_3$ |
| 3 | p. OCH$_3$ |
| 3 | p.OH |
| 4 | H |
| 4 | p.CH$_3$ |
| 6 | H | c) Preparation of compounds of the general formula C:

35 g (0.173 mol) of 2-(3-phenylpropionyl)-thiophene and 27.05 g (0.190 mol) of 3,3-dimethylglutaric anhydride are dissolved in 500 ml of nitrobenzene. The temperature of the reaction medium is adjusted to 0° C. and 57.67 g (0.433 mol) of aluminum chloride are added in portions while stirring vigorously and maintaining the temperature at 5° C.

After 1 hour at 5° C., stirring is continued for 12 hours at room temperature.

The mixture is poured onto 500 g of ice to which 50 ml of concentrated HCl have been added. The hydrolysis is continued for 2 hours with stirring, then the organic phase is largely decanted off and the nitrobenzene steam distilled off.

The acid is extracted 3 times with 100 ml of ether each time, the organic phase is dried over MgSO$_4$ and the solvent is distilled off. The residue is dissolved in 200 ml of saturated sodium bicarbonate solution, extracted with 50 ml of ether and decolourised with animal black. The aqueous solution is acidified with aqueous 4 N HCl and extracted 3 times with 100 ml of ether each time. The organic phase is washed with aqueous 1 N HCl, then with water, and dried for 3 hours over MgSO$_4$. The solvent is distilled off leaving 55 g of a pale-yellow oil which slowly crystallises to give 5-(3-phenylpropionyl)-2-(3,3-dimethylglutaryl)-thiophene.

The products listed in the following Table 3 were also prepared in this manner.

TABLE 3 compounds of the formula

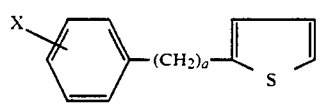

| X | a | b | c | R$_1$ | R$_2$ |
|---|---|---|---|---|---|
| H | 2 | 2 | 2 | CH$_3$ | CH$_3$ |
| p.CH$_3$ | 2 | 2 | 2 | CH$_3$ | CH$_3$ |
| H | 3 | 2 | 2 | H | H |
| p.CH$_3$ | 3 | 2 | 2 | H | H |
| H | 3 | 2 | 2 | CH$_3$ | H |
| p.CH$_3$ | 3 | 2 | 2 | CH$_3$ | H |
| H | 3 | 2 | 2 | CH$_3$ | CH$_3$ |
| p.CH$_3$ | 3 | 2 | 2 | CH$_3$ | CH$_3$ |
| m.CH$_3$ | 3 | 2 | 2 | CH$_3$ | CH$_3$ |

TABLE 3-continued compounds of the formula

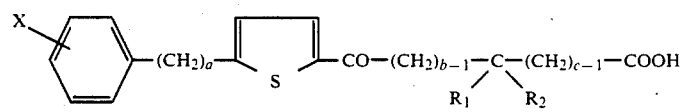

| X | a | b | c | R₁ | R₂ |
|---|---|---|---|-----|-----|
| H | 3 | 2 | 2 | | |

| X | a | b | c | R₁ | R₂ |
|------|---|---|---|-----|-----|
| H | 3 | 3 | 1 | CH₃ | CH₃ |
| p.CH₃ | 3 | 3 | 1 | CH₃ | CH₃ |
| H | 4 | 2 | 2 | CH₃ | CH₃ |
| p.CH₃ | 4 | 2 | 2 | CH₃ | CH₃ |
| H | 6 | 2 | 2 | CH₃ | CH₃ | d) Preparation of compounds of the general formula II:

50 g (0.145 mol) of 5-(3-phenylpropionyl)-2-(3,3-dimethylglutaryl)-thiophene are dissolved in 250 ml of triethylene glycol.

The temperature is adjusted to 70° C. and 28.5 mg (0.536 mol) of hydrazine hydrate (80%) are added.

The temperature is increased to 100° C. and 24.4 g (0.435 mol) of potassium hydroxide are added. Refluxing is maintained for 45 minutes, then the water is distilled off until the temperature reaches 210°-220° C.

Refluxing is then continued for 2 hours.

The reaction medium is hydrolysed with 300 ml of water to which 35 ml of concentrated HCl have been added, and is then extracted three times with 100 ml of ether each time.

The organic phase is washed with aqueous N HCl then with water, dried over MgSO₄ and decolourised with animal black.

The solvent is distilled off leaving 41.5 g of colourless oil which slowly crystallises to give 5-(3-phenylpropionyl)-2-(4-carboxy-3,3-dimethylbutaryl)-thiophene.

The products listed in the following Table 4 were prepared in this manner:

TABLE 4 compounds of formula

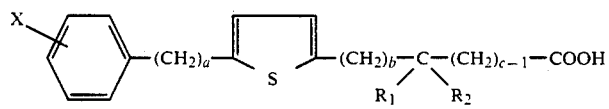

| X | a | b | c | R₁ | R₂ |
|------|---|---|---|-----|-----|
| H | 2 | 2 | 2 | CH₃ | CH₃ |
| p.CH₃ | 2 | 2 | 2 | CH₃ | CH₃ |
| H | 3 | 2 | 2 | H | H |
| p.CH₃ | 3 | 2 | 2 | H | H |
| H | 3 | 2 | 2 | CH₃ | H |
| p.CH₃ | 3 | 2 | 2 | CH₃ | H |
| H | 3 | 2 | 2 | CH₃ | CH₃ |
| p.CH₃ | 3 | 2 | 2 | CH₃ | CH₃ |
| m.CH₃ | 3 | 2 | 2 | CH₃ | CH₃ |
| H | 3 | 2 | 2 | | |

| X | a | b | c | R₁ | R₂ |
|------|---|---|---|-----|-----|
| H | 3 | 3 | 1 | CH₃ | CH₃ |
| p.CH₃ | 3 | 3 | 1 | CH₃ | CH₃ |
| H | 4 | 2 | 2 | CH₃ | CH₃ |
| p.CH₃ | 4 | 2 | 2 | CH₃ | CH₃ |
| H | 6 | 2 | 2 | CH₃ | CH₃ |

B) Second method:

a) Preparation of compounds of the general formula D:

42.07 g (0.5 mol) of thiophene and 71.07 g (0.55 mol) of 3,3-dimethylglutaric anhydride are dissolved in 1550 ml of nitrobenzene. The reaction mixture is cooled to 0°-2° C. with a brine bath and 166.67 g (1.25 mol) of aluminum chloride are added in portions while stirring vigorously and maintaining the temperature of the reaction mixture at a value lower than 5° C. The reaction is continued for 30 minutes at a temperature of 0°-5° C. and is then completed at room temperature over a period of 10 hours.

The reaction mixture is hydrolysed with 3 l of a water/ice mixture. After the addition of 217 ml of concentrated HCl, the organic phase is decanted off, the nitrobenzene is steam distilled off and the residual aqueous phase is extracted 3 times with 200 ml of ethyl ether each time. The combined ethereal phases are washed with a normal aqueous solution of HCl and then with water. After treating with magnesium sulfate and animal black, the solvents are distilled off leaving 106.5 g of a pale-yellow oil which slowly crystallises (yield: 94%).

The product can be recrystallised in water to yield, after filtration and drying, 2-(3,3-dimethylglutaryl)-thiophene in the form of a white solid, M.p.: 70° C.

The products listed in the following Table 5 were prepared in this manner:

TABLE 5 compounds of formula

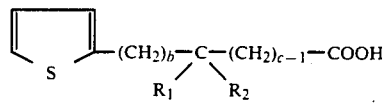

| b | c | $R_1$ | $R_2$ |
|---|---|-------|-------|
| 2 | 2 | $CH_3$ | $CH_3$ |
| 2 | 2 | $CH_3$ | H |
| 2 | 2 | H | H |
| 1 | 3 | $CH_3$ | $CH_3$ |
| 3 | 1 | $CH_3$ | $CH_3$ | b) Preparation of compounds of the general formula E:

17.5 g (0.0773 mol) of 2-(3,3-dimethylglutaryl)-thiophene are suspended in 100 ml of triethylene glycol. The temperature is adjusted to 70° C. and stirring is continued until dissolution is complete. 10.83 g (0.27 mol) of 80% hydrazine hydrate are added. The temperature is increased to 100° C. then 13 g (0.23 mol) of potassium hydroxide pellets are added.

Refluxing is maintained for 30 minutes then the water that has formed is distilled off over approximately one hour; the temperature rises to 200°-210° C., and the reaction is complete after one hour at that temperature.

After The reaction medium has been cooled to 20° C., it is hydrolysed with 300 ml of water and neutralised with concentrated hydrochloric acid.

The aqueous phase is extracted 3 times with 100 ml of ethyl ether each time and then the ethereal phases are washed with a normal aqueous solution of HCl, then with water. After treatment with anhydrous magnesium sulphate and animal black, the solvent is distilled off leaving 14.37 g of a pale-yellow oil which slowly crystallises to give 5-(2-thienyl)-3,3-dimethylpentanoic acid. Yield: 80%.

The products listed in the following Table 6 were prepared in this manner:

TABLE 6 compounds of formula

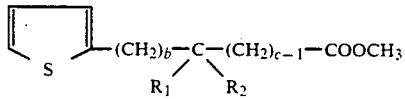

| b | c | $R_1$ | $R_2$ |
|---|---|-------|-------|
| 2 | 2 | $CH_3$ | $CH_3$ |
| 2 | 2 | $CH_3$ | H |
| 2 | 2 | H | H |

TABLE 6-continued compounds of formula

| b | c | $R_1$ | $R_2$ |
|---|---|-------|-------|
| 1 | 3 | $CH_3$ | $CH_3$ |
| 3 | 1 | $CH_3$ | $CH_3$ | c) Preparation of compounds of the general formula F:

13 g (0.0612 mol) of 5-(2-thienyl)-3,3-dimethylpentanoic acid are dissolved in 200 ml of anhydrous methanol in the presence of a catalytic amount (0.025 g) of p-toluenesulphonic acid.

The mixture is heated to and then maintained at reflux for 20 hours. After verifying the absence of the starting acid (by thin layer chromatography), the methanol is distilled off and the residue is taken up in ethyl ether. After washing the ethereal phase with water, treating with anhydrous $MgSO_4$ and then animal black, the solvent is distilled off leaving a crude oil which is chromatographed ($SiO_2/CH_2Cl_2$) to yield 12.25 g of a colourless oil. Yield: 88%.

The methyl esters of the acids of Table 6, that is to say the produces listed in the following Table 7, were prepared in this manner:

TABLE 7 compounds of formula

| b | c | $R_1$ | $R_2$ |
|---|---|-------|-------|
| 2 | 2 | $CH_3$ | $CH_3$ |
| 2 | 2 | $CH_3$ | H |
| 2 | 2 | H | H |
| 1 | 3 | $CH_3$ | $CH_3$ |
| 3 | 1 | $CH_3$ | $CH_3$ | d) Preparation of compounds of the general formula G:

7 g (0.0309 mol) of 5-(2-thienyl)-3,3-dimethylpentanoic acid methyl ester and an equivalent of p-fluorophenylpropanoic acid chloride - prepared from 5.2 g (0.0309 mol) of p-fluorophenylpropanoic acid and 3.36 ml of $SOCl_2$ - are dissolved in 175 ml of anhydrous methylene chloride. 4.52 ml (0.0386 mol) of tin chloride are added drop by drop, with vigorous stirring, to the solution maintained at 0° C. The reaction is complete after 30 minutes at 0° C. and then one night at room temperature.

The reaction mixture is hydrolysed with 500 ml of a water/ice mixture acidified with 50 ml of concentrated HCl. After stirring for 4 hours, the organic phase is decanted off and the aqueous phase is extracted 3 times with 100 ml of dichloromethane each time.

The organic phases are washed with a normal aqueous solution of HCl, a saturated aqueous solution of sodium bicarbonate and then water, and are then treated with $MgSO_4$ and animal black and concentrated to dryness to give 11.06 g of a crude oil with, after chromatography (SiO$_2$/CH$_2$Cl$_2$), yields 10.48 g of a colourless oil. Yield: 90.5%.

The products listed in the following Table 8 were prepared in this manner:

TABLE 8 compounds of formula

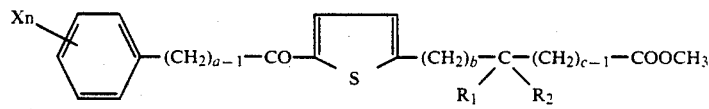

| Xn | a | b | c | R$_1$ | R$_2$ |
|---|---|---|---|---|---|
| H | 3 | 2 | 2 | CH$_3$ | CH$_3$ |
| p.F | 3 | 2 | 2 | CH$_3$ | CH$_3$ |
| p.F | 3 | 2 | 2 | CH$_3$ | H |
| m.F | 3 | 2 | 2 | CH$_3$ | CH$_3$ |
| o.Cl | 3 | 2 | 2 | CH$_3$ | CH$_3$ |
| H | 6 | 2 | 2 | CH$_3$ | CH$_3$ |
| 2,4 diCH$_3$ | 3 | 2 | 2 | CH$_3$ | H |
| 2,4 diCH$_3$ | 3 | 2 | 2 | CH$_3$ | CH$_3$ |
| m.F | 3 | 2 | 2 | CH$_3$ | H |
| p.CH$_3$ | 4 | 2 | 2 | CH$_3$ | H |
| p.CH$_3$ | 4 | 2 | 2 | CH$_3$ | CH$_3$ |
| 2,5 diCH$_3$ | 3 | 2 | 2 | CH$_3$ | CH$_3$ |
| 2,5 diCH$_3$ | 3 | 2 | 2 | CH$_3$ | H |
| p.CH$_3$ | 3 | 2 | 2 | H | H |
| p.CH$_3$ | 3 | 1 | 3 | CH$_3$ | CH$_3$ |
| p.CH$_3$ | 3 | 3 | 1 | CH$_3$ | CH$_3$ |
| p.-CH(CH$_3$)$_2$ | 3 | 2 | 2 | CH$_3$ | H |
| p.-CH(CH$_3$)$_2$ | 3 | 2 | 2 | CH$_3$ | CH$_3$ |
| p.-(CH$_2$)$_4$—CH$_3$ | 3 | 2 | 2 | CH$_3$ | H |
| p.-(CH$_2$)$_4$—CH$_3$ | 3 | 2 | 2 | CH$_3$ | CH$_3$ |
| 3-F,4-CH$_3$ | 3 | 2 | 2 | CH$_3$ | H |
| 3-F,4-CH$_3$ | 3 | 2 | 2 | CH$_3$ | CH$_3$ | e) Preparation of compounds of the general formula II:

10.48 g (0.0278 mol) of methyl 5-[5-(3-p-fluorophenylpropionyl)-2-thienyl]-3,3-dimethyl pentanoate are dissolved in 80 ml of triethylene glycol heated to 70° C. 3.12 g (0.0974 mol) of 80% hydrazine hydrate are added.

The temperature is increased to 100° C. and 4.68 g (0.083 mol) of potassium hydroxide pellets are added in one batch. After refluxing for 30 minutes, the water that has formed is distilled off over a period of one hour during which the temperature rises to 210°-220° C. After one hour at that temperature the reaction is complete.

After having been cooled to 20° C., the reaction mixture is hydrolysed with 200 ml of water acidified by 30 ml of concentrated HCl, and extracted 3 times with 100 ml of sulphuric ether each time. The combined ethereal phases are washed with a normal HCL solution and then with water, and treated with anhydrous MgSO$_4$ then animal black and concentrated to dryness.

10.5 g of crude oil are obtained which are chromatographed (SiO$_2$/CH$_2$Cl$_2$) to yield 9.10 g of a colourless oil. Yield: 94%.

The products listed in the following Table 9 were prepared in this manner:

TABLE 9 compounds of formula

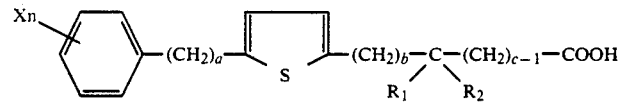

| Xn | a | b | c | R$_1$ | R$_2$ |
|---|---|---|---|---|---|
| H | 3 | 2 | 2 | CH$_3$ | CH$_3$ |
| p.F | 3 | 2 | 2 | CH$_3$ | CH$_3$ |
| p.F | 3 | 2 | 2 | CH$_3$ | H |
| m.F | 3 | 2 | 2 | CH$_3$ | CH$_3$ |
| o.Cl | 3 | 2 | 2 | CH$_3$ | CH$_3$ |
| H | 6 | 2 | 2 | CH$_3$ | CH$_3$ |
| 2,4-diCH$_3$ | 3 | 2 | 2 | CH$_3$ | H |
| 2,4-diCH$_3$ | 3 | 2 | 2 | CH$_3$ | CH$_3$ |
| m.F | 3 | 2 | 2 | CH$_3$ | H |
| p.CH$_3$ | 4 | 2 | 2 | CH$_3$ | H |
| p.CH$_3$ | 4 | 2 | 2 | CH$_3$ | CH$_3$ |
| 2,5-diCH$_3$ | 3 | 2 | 2 | CH$_3$ | CH$_3$ |
| 2,5-diCH$_3$ | 3 | 2 | 2 | CH$_3$ | H |
| p.CH$_3$ | 3 | 2 | 2 | H | H |
| p.CH$_3$ | 3 | 1 | 3 | CH$_3$ | CH$_3$ |
| p.CH$_3$ | 3 | 3 | 1 | CH$_3$ | CH$_3$ |
| p.-CH(CH$_3$)$_2$ | 3 | 2 | 2 | CH$_3$ | H |
| p.-CH(CH$_3$)$_2$ | 3 | 2 | 2 | CH$_3$ | CH$_3$ |

TABLE 9-continued compounds of formula

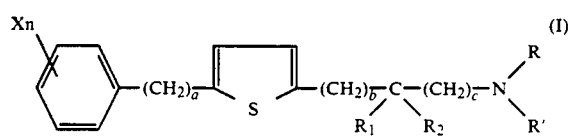

| Xn | a | b | c | R₁ | R₂ |
|---|---|---|---|---|---|
| p.-(CH₂)₄—CH₃ | 3 | 2 | 2 | CH₃ | H |
| p.-(CH₂)₄—CH₃ | 3 | 2 | 2 | CH₃ | CH₃ |
| 3-F, 4-CH₃ | 3 | 2 | 2 | CH₃ | H |
| 3-F, 4-CH₃ | 3 | 2 | 2 | CH₃ | CH₃ |

II) Synthesis of compounds of the general formula I:

(I)

A) Preparation of compounds of the general formula V:

16.5 g (0.05 mol) of 5-(3-phenylpropyl)-2-(4-carboxy-3,3-dimethylbutyl)-thiophene and 6.5 g (0.055 mol) of thionyl chloride are dissolved in 300 ml of anhydrous chloroform and stirring is maintained until the evolution of gas has ceased. The solvent and excess thionyl chloride are then distilled off under reduced pressure.

The acid chloride so-obtained dissolved in 250 ml of anhydrous ether, and 8.71 g (0.1 mol) of morpholine dissolved in 150 ml of anhydrous ether, are simultaneously poured into 100 ml of anhydrous ether agitated magnetically.

After 20 minutes, the morpholinium hydrochloride formed is filtered off and washed with ether.

The ethereal phase is washed twice with 30 ml of water each time, dried over MgSO₄ and decolourised with animal black.

The solvent is evaporated off to leave 18.8 g of a colourless oil: 5-(3-phenylpropyl)-(2-(3,3-dimethyl-4-N-morpholinocarbonylbutyl-thiophene. 5-(3-phenylpropyl)-2-(4-N-morpholinocarbonyl-3,3-dimethylbutyl)-thiophene)

The products listed in the following Table 10 were prepared in this manner:

TABLE 10 compounds of formula

| Xn | a | b | c | R₁ | R₂ | −N(R)(R') |
|---|---|---|---|---|---|---|
| H | 2 | 2 | 2 | CH₃ | CH₃ | −N(morpholino) |
| p.CH₃ | 2 | 2 | 2 | CH₃ | H | −N(piperazinyl)-N-CH₂-(2,3,4-trimethoxyphenyl) |
| p.CH₃ | 2 | 2 | 2 | CH₃ | CH₃ | −N(morpholino) |
| p.CH₃ | 2 | 2 | 2 | CH₃ | CH₃ | −N(piperazinyl)-N-CH₂-(2,3,4-trimethoxyphenyl) |

TABLE 10-continued
compounds of formula
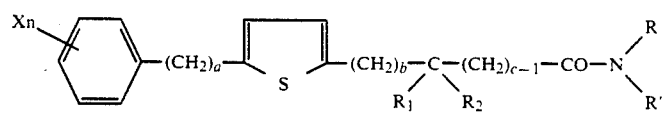
| Xn | a | b | c | R₁ | R₂ | -NRR' |
|---|---|---|---|---|---|---|
| H | 3 | 2 | 2 | H | H | -N(morpholino) |
| p.CH₃ | 3 | 2 | 2 | H | H | -N(morpholino) |
| H | 3 | 2 | 2 | CH₃ | H | -N(morpholino) |
| p.CH₃ | 3 | 2 | 2 | CH₃ | H | -N(morpholino) |
| p.F | 3 | 2 | 2 | CH₃ | H | -N(morpholino) |
| H | 3 | 2 | 2 | CH₃ | CH₃ | -N(morpholino) |
| p.CH₃ | 3 | 2 | 2 | CH₃ | CH₃ | -N(morpholino) |
| m.CH₃ | 3 | 2 | 2 | CH₃ | CH₃ | -N(morpholino) |
| p.F | 3 | 2 | 2 | CH₃ | CH₃ | -N(morpholino) |
| m.F | 3 | 2 | 2 | CH₃ | CH₃ | -N(morpholino) |
| 2,4 diCH₃ | 3 | 2 | 2 | CH₃ | H | -N(piperazinyl)-CH₂-(2,3,4-triOCH₃-phenyl) |

TABLE 10-continued compounds of formula $$Xn-\text{Ph}-(CH_2)_a-\underset{S}{\text{thiophene}}-(CH_2)_b-\underset{R_1\ R_2}{C}-(CH_2)_{c-1}-CO-N\underset{R'}{\overset{R}{\diagup}}$$

| Xn | a | b | c | R₁ | R₂ | $-N\overset{R}{\underset{R'}{\diagup}}$ |
|---|---|---|---|---|---|---|
| 2,4 diCH₃ | 3 | 2 | 2 | CH₃ | CH₃ | piperazinyl-CH₂-(2,3,4-triOCH₃-phenyl) |
| 2,5 diCH₃ | 3 | 2 | 2 | CH₃ | H | piperazinyl-CH₂-(2,3,4-triOCH₃-phenyl) |
| 2,5 diCH₃ | 3 | 2 | 2 | CH₃ | CH₃ | piperazinyl-CH₂-(2,3,4-triOCH₃-phenyl) |
| p.CH₃ | 4 | 2 | 2 | CH₃ | H | piperazinyl-CH₂-(2,3,4-triOCH₃-phenyl) |
| p.CH₃ | 4 | 2 | 2 | CH₃ | CH₃ | piperazinyl-CH₂-(2,3,4-triOCH₃-phenyl) |
| O.cl | 3 | 2 | 2 | CH₃ | CH₃ | morpholinyl |
| H | 3 | 2 | 2 | \-cyclopentyl (R₁R₂ joined)\- |  | morpholinyl |
| H | 3 | 2 | 2 | CH₃ | CH₃ | $-NH_2$ |
| H | 3 | 2 | 2 | CH₃ | CH₃ | $-N(CH_3)_2$ |
| H | 3 | 2 | 2 | CH₃ | CH₃ | piperidinyl |

TABLE 10-continued compounds of formula

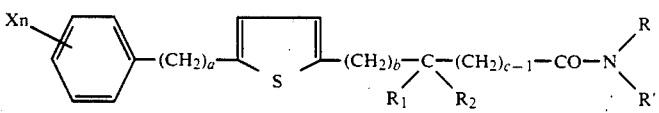

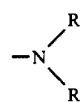

| Xn | a | b | c | $R_1$ | $R_2$ | $-N\begin{matrix}R\\R'\end{matrix}$ |
|---|---|---|---|---|---|---|
| H | 3 | 2 | 2 | $CH_3$ | $CH_3$ | -N(piperazine)N-$CH_2$-(2,3,4-tri-$OCH_3$-phenyl) |
| m.F | 3 | 2 | 2 | $CH_3$ | $CH_3$ | -N(piperazine)N-$CH_2$-(2,3,4-tri-$OCH_3$-phenyl) |
| m.F | 3 | 2 | 2 | $CH_3$ | H | -N(piperazine)N-$CH_2$-(2,3,4-tri-$OCH_3$-phenyl) |
| p.F | 3 | 2 | 2 | $CH_3$ | $CH_3$ | -N(piperazine)N-$CH_2$-(2,3,4-tri-$OCH_3$-phenyl) |
| p-$CH_3$ | 3 | 2 | 2 | $CH_3$ | $CH_3$ | -N(piperazine)N-$CH_2$-(2,3,4-tri-$OCH_3$-phenyl) |
| H | 3 | 3 | 1 | $CH_3$ | $CH_3$ | -N(morpholine) |
| p.$CH_3$ | 3 | 3 | 1 | $CH_3$ | $CH_3$ | -N(morpholine) |
| H | 4 | 2 | 2 | $CH_3$ | $CH_3$ | -N(morpholine) |
| p.$CH_3$ | 4 | 2 | 2 | $CH_3$ | $CH_3$ | -N(morpholine) |
| H | 6 | 2 | 2 | $CH_3$ | $CH_3$ | -N(morpholine) |

TABLE 10-continued compounds of formula

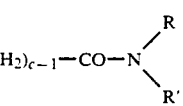

| Xn | a | b | c | R₁ | R₂ | −N(R)(R') |
|---|---|---|---|---|---|---|
| H | 6 | 2 | 2 | CH₃ | CH₃ | piperazinyl-CH₂-(2,3,4-trimethoxyphenyl) |
| p.CH₃ | 3 | 2 | 2 | H | H | piperazinyl-CH₂-(2,3,4-trimethoxyphenyl) |
| p.CH₃ | 3 | 1 | 3 | CH₃ | CH₃ | " |
| p.CH₃ | 3 | 3 | 1 | CH₃ | CH₃ | " |
| p.CH₃ | 3 | 1 | 3 | CH₃ | CH₃ | morpholino |
| p.-CH(CH₃)₂ | 3 | 2 | 2 | CH₃ | H | piperazinyl-CH₂-(2,3,4-trimethoxyphenyl) |
| p.-CH(CH₃)₂ | 3 | 2 | 2 | CH₃ | CH₃ | " |
| p.-CH(CH₃)₂ | 3 | 2 | 2 | CH₃ | H | morpholino |
| p.-CH(CH₃)₂ | 3 | 2 | 2 | CH₃ | CH₃ | " |
| 3-F, 4-CH₃ | 3 | 2 | 2 | CH₃ | H | piperazinyl-CH₂-(2,3,4-trimethoxyphenyl) |
| 3-F, 4-CH₃ | 3 | 2 | 2 | CH₃ | CH₃ | " |
| p.-(CH₂)₄—CH₃ | 3 | 2 | 2 | CH₃ | H | morpholino |
| p.-(CH₂)₄—CH₃ | 3 | 2 | 2 | CH₃ | CH₃ | " |
| p.-(CH₂)₄—CH₃ | 3 | 2 | 2 | CH₃ | H | piperazinyl-CH₂-(2,3,4-trimethoxyphenyl) |
| p.-(CH₂)₄—CH₃ | 3 | 2 | 2 | CH₃ | CH₃ | " |

B) Preparation of compounds of the general formula I:

Refluxing is maintained for 2 hours after the addition, then the reaction mixture is cooled to 20° C. and carefully hydrolysed with 4 ml of water, 4 ml of 4 N aqueous sodium hydroxide solution, then 8 ml of water. The solid formed is distilled off and washed with ether.

The ethereal phase is washed with 3 times with 50 ml of water, dried over MgSO₄, decolourised with animal black and concentrated to dryness.

The residue is chromatographed on SiO₂ (solvent: $CH_2Cl_2$—$CH_3COOC_2H_5$, 95:5).

The fractions containing the amine are concentrated to dryness. The residue is taken up in 600 ml of anhydrous ether and the hydrochloride is obtained by the addition of an equivalent of HCl dissolved in ether.

After stirring for one hour, the hydrochloride is filtered off, washed with ether, suction-filtered and dried in vacuo. 16 g of 5-(3-phenylpropyl)-(2-(3,3-dimethyl-5-N-morpholinopentyl)-thiophene hydrochloride are obtained in the form of a white solid (cf. Example 8 of Table 11 below).

The products corresponding to Examples 1 to 51 listed in the following Table 11 were prepared in this manner:

TABLE 11 compounds of formula:

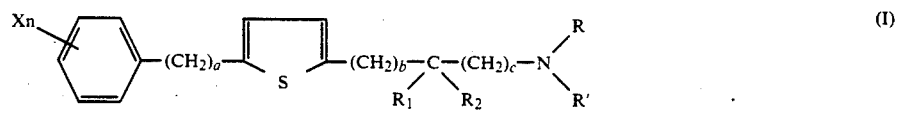

(I)

| Example No. | X | n | a | b | c | $R_1$ | $R_2$ | $-N\begin{smallmatrix}R\\R'\end{smallmatrix}$ | form isolated | M.p. °C. (Kofler) |
|---|---|---|---|---|---|---|---|---|---|---|
| 1 | H | 1 | 2 | 2 | 2 | CH₃ | CH₃ | −N⌒O (morpholino) | HCl | 210 |
| 2 | p.CH₃ | 1 | 2 | 2 | 2 | CH₃ | CH₃ | −N⌒O | HCl | 220-222 |
| 3 | H | 1 | 3 | 2 | 2 | H | H | −N⌒O | CH₃SO₃H | 81 |
| 4 | p.CH₃ | 1 | 3 | 2 | 2 | H | H | −N⌒O | HCl | 112-113 |
| 5 | H | 1 | 3 | 2 | 2 | CH₃ | H | −N⌒O | HCl | 146-148 |
| 6 | p.CH₃ | 1 | 3 | 2 | 2 | CH₃ | H | −N⌒O | HCl | 150-152 |
| 7 | p.F | 1 | 3 | 2 | 2 | CH₃ | H | −N⌒O | HCl | 146 |
| 8 | H | 1 | 3 | 2 | 2 | CH₃ | CH₃ | −N⌒O | CH₃SO₃H | ≈100 |
| 9 | p.CH₃ | 1 | 3 | 2 | 2 | CH₃ | CH₃ | −N⌒O | HCl | 207-208 |

TABLE 11-continued compounds of formula:

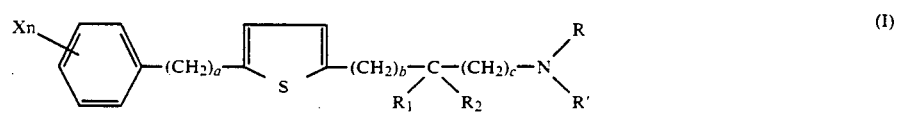
(I)

| Example No. | X | n | a | b | c | R₁ | R₂ | $-N\begin{matrix}R\\R'\end{matrix}$ | form isolated | M.p. °C. |
|---|---|---|---|---|---|---|---|---|---|---|
| 10 | m.CH₃ | 1 | 3 | 2 | 2 | CH₃ | CH₃ | −N⌒O (morpholino) | HCl | ≃206 |
| 11 | p.F | 1 | 3 | 2 | 2 | CH₃ | CH₃ | −N⌒O (morpholino) | HCl | 195–200 |
| 12 | m.F | 1 | 3 | 2 | 2 | CH₃ | CH₃ | −N⌒O (morpholino) | HCl | 190 |
| 13 | o.Cl | 1 | 3 | 2 | 2 | CH₃ | CH₃ | −N⌒O (morpholino) | HCl | 205 |
| 14 | H | 1 | 3 | 2 | 2 | \-(cyclopentyl R₁R₂)- | | −N⌒O (morpholino) | HCl | 166–168 |
| 15 | H | 1 | 3 | 2 | 2 | CH₃ | CH₃ | −NH₂ | HCl | 108 |
| 16 | H | 1 | 3 | 2 | 2 | CH₃ | CH₃ | −N(CH₃)₂ | HCl | 170 |
| 17 | H | 1 | 3 | 2 | 2 | CH₃ | CH₃ | −N(piperidino) | HCl | 110–112 |
| 18 | H | 1 | 3 | 2 | 2 | CH₃ | CH₃ | −N(piperazinyl)−CH₂−(2,3,4-triOCH₃-phenyl) | 2 HCl | 206 |
| 19 | m.F | 1 | 3 | 2 | 2 | CH₃ | CH₃ | −N(piperazinyl)−CH₂−(2,3,4-triOCH₃-phenyl) | 2 HCl | 207 |
| 20 | p.F | 1 | 3 | 2 | 2 | CH₃ | CH₃ | −N(piperazinyl)−CH₂−(2,3,4-triOCH₃-phenyl) | 2 HCl | 235 |

TABLE 11-continued compounds of formula:

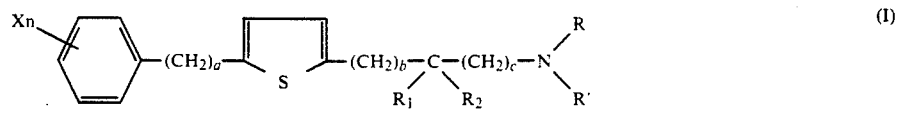

| Example No. | X | n | a | b | c | $R_1$ | $R_2$ | $-N\begin{matrix}R\\R'\end{matrix}$ | form isolated | M.p. °C. |
|---|---|---|---|---|---|---|---|---|---|---|
| 21 | H | 1 | 3 | 3 | 1 | $CH_3$ | $CH_3$ | −N⟨morpholine⟩O | HCl | 108–110 |
| 22 | p.$CH_3$ | 1 | 3 | 3 | 1 | $CH_3$ | $CH_3$ | −N⟨morpholine⟩O | HCl | 128–130 |
| 23 | H | 1 | 4 | 2 | 2 | $CH_3$ | $CH_3$ | −N⟨morpholine⟩O | HCl | 194–196 |
| 24 | p.$CH_3$ | 1 | 4 | 2 | 2 | $CH_3$ | $CH_3$ | −N⟨morpholine⟩O | HCl | 192–194 |
| 25 | H | 1 | 6 | 2 | 2 | $CH_3$ | $CH_3$ | −N⟨morpholine⟩O | HCl | 197 |
| 26 | p.$CH_3$ | 1 | 3 | 2 | 2 | $CH_3$ | $CH_3$ | −N⟨piperazine⟩N−$CH_2$−(2,3,4-tri$OCH_3$-phenyl) | 2 HCl | (capillary tube) 210 |
| 27 | m.F | 1 | 3 | 2 | 2 | $CH_3$ | H | " | 2 HCl | 190 |
| 28 | p.$CH_3$ | 1 | 3 | 2 | 2 | $CH_3$ | H | " | 2 HCl | 188–190 |
| 29 | p.$CH_3$ | 1 | 2 | 2 | 2 | $CH_3$ | H | " | 2 HCl | 198–202 |
| 30 | p.$CH_3$ | 1 | 2 | 2 | 2 | $CH_3$ | $CH_3$ | " | 2 HCl | 225–230 |
| 31 | H | 1 | 6 | 2 | 2 | $CH_3$ | $CH_3$ | " | 2 HCl | >240 (dec) |
| 32 | 2,4 di$CH_3$ | 2 | 3 | 2 | 2 | $CH_3$ | H | " | 2 HCl | 230–235 |
| 33 | 2,4 di$CH_3$ | 2 | 3 | 2 | 2 | $CH_3$ | $CH_3$ | " | 2 HCl | 235 |
| 34 | 2,5 di$CH_3$ | 2 | 3 | 2 | 2 | $CH_3$ | H | " | | |
| 35 | 2,5 di$CH_3$ | 2 | 3 | 2 | 2 | $CH_3$ | $CH_3$ | " | | |
| 36 | p.$CH_3$ | 1 | 4 | 2 | 2 | $CH_3$ | H | " | 2 HCl | 227–230 |
| 37 | p.$CH_3$ | 1 | 4 | 2 | 2 | $CH_3$ | $CH_3$ | −N⟨piperazine⟩N−$CH_2$−(2,3,4-tri$OCH_3$-phenyl) | 2 HCl | 238–240 |
| 38 | p.$CH_3$ | 1 | 3 | 2 | 2 | H | H | " | 2 HCl | 212–214 |
| 39 | p.$CH_3$ | 1 | 3 | 1 | 3 | $CH_3$ | $CH_3$ | " | 2 HCl | 225–230 |
| 40 | p.$CH_3$ | 1 | 3 | 3 | 1 | $CH_3$ | $CH_3$ | " | | |
| 41 | p.$CH_3$ | 1 | 3 | 1 | 3 | $CH_3$ | $CH_3$ | −N⟨morpholine⟩O | | |

TABLE 11-continued compounds of formula:

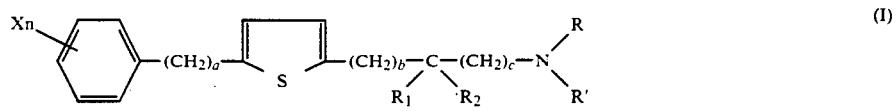

| Example No. | X | n | a | b | c | $R_1$ | $R_2$ | $\overset{R}{-N\diagdown R'}$ | form isolated | M.p. °C. |
|---|---|---|---|---|---|---|---|---|---|---|
| 42 | p.-CH(CH$_3$)$_2$ | 1 | 3 | 2 | 2 | CH$_3$ | H | -N(piperazinyl)-N-CH$_2$-C$_6$H$_2$(OCH$_3$)$_3$ (H$_3$CO, OCH$_3$, OCH$_3$) | | |
| 43 | p.-CH(CH$_3$)$_2$ | 1 | 3 | 2 | 2 | CH$_3$ | CH$_3$ | " | | |
| 44 | p.-CH(CH$_3$)$_2$ | 1 | 3 | 2 | 2 | CH$_3$ | H | -N(morpholinyl) | HCl | 170 |
| 45 | p.-CH(CH$_3$)$_2$ | 1 | 3 | 2 | 2 | CH$_3$ | CH$_3$ | " | HCl | 210 |
| 46 | 3-F, 4-CH$_3$ | 2 | 3 | 2 | 2 | CH$_3$ | H | -N(piperazinyl)-N-CH$_2$-C$_6$H$_2$(OCH$_3$)$_3$ | 2 HCl | 195–198 |
| 47 | 3-F, 4-CH$_3$ | 2 | 3 | 2 | 2 | CH$_3$ | CH$_3$ | " | | |
| 48 | p.-(CH$_2$)$_4$—CH$_3$ | 1 | 3 | 2 | 2 | CH$_3$ | H | -N(morpholinyl) | | |
| 49 | p.-(CH$_2$)$_4$—CH$_3$ | 1 | 3 | 2 | 2 | CH$_3$ | CH$_3$ | | | |
| 50 | p.-(CH$_2$)$_4$—CH$_3$ | 1 | 3 | 2 | 2 | CH$_3$ | H | -N(piperazinyl)-N-CH$_2$-C$_6$H$_2$(OCH$_3$)$_3$ | 2 HCl | 220–225 (dec) |
| 51 | p.-(CH$_2$)$_4$—CH$_3$ | 1 | 3 | 2 | 2 | CH$_3$ | CH$_3$ | " | 2 HCl | >240 (dec) |

We claim:

1. Amides of the formula V:

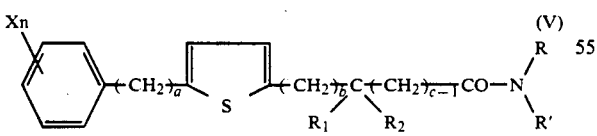

in which X, n, a, b, c, $R_1$, $R_2$, R and R' are as defined as follows:

X is selected from the group consisting of: a hydrogen atom, halogen atoms, straight-chain and branched alkyl and alkoxy radicals each having from 1 to 5 carbon atoms, and dialkylamino radicals in which each alkyl group has from 1 to 5 carbon atoms;

n is selected from the group consisting of: 1 and 2;

a is selected from the group consisting of: integers of from 2 to 6 inclusive;

b is selected from the group consisting of: 2 and 3;

c is selected from the group consisting of: 1 and 2, and is such that b+c=4;

$R_1$ and $R_2$, which may be the same or different, are each selected from the group consisting of: a hydrogen atom and alkyl radicals having from 1 to 5 carbon atoms, and $R_1$ and $R_2$ together with the carbon atom to which they are bonded form a hydrocarbon ring having from 3 to 6 carbon atoms inclusive; and R and R', which may be the same or different, are each selected from the group consisting of: a hydrogen atom and alkyl radicals having from 1 to 5 carbon atoms, and R and R' together with the nitrogen atom to which the are bonded form a heterocyclic radical selected from the group consisting of -5- and 6-membered heterocyclic radicals each having in addition to carbon atoms only one nitrogen atom, one nitrogen atom and one oxygen atom, or two nitrogen atoms, and each of these heterocyclic radicals substituted by a substituant selected from the group consisting of: straight-chain and branched alkyl radicals having from 1 to 5 carbon atoms inclusive and arylalkyl, haloarylkyl, ($C_1$–$C_5$)alkyl-arylalkyl and ($C_1$–$C_5$)alkoxy-arylakyl radicals, in which the alkyl moiety of each aryl-alkyl radical has from 1 to 5 carbon atoms inclusive.

2. A compound of claim 1 which is: 5-(3-p-isopropyl-phenylpropyl)-2-{4-[4(2,3,4-trimethoxybenzyl)-piperazin-1-yl carbonyl]-3,3-dimethylbutyl}-thiophene.

3. A compound of claim 1 which is: 5-(3-p-pentyl-phenylpropyl)-2-{4-[4(2,3,4-trimethoxybenzyl)-piperazin-1-yl carbonyl]-3,3-dimethylbutyl}-thiophene.

4. A compound of claim 1 which is: 5-(3-metra-fluorophenylpropyl)-2-{4-[4(2,3,4-trimethoxybenzyl)-piperazin-1-yl carbonyl]-3-methylbutyl}-thiophene.

5. A compound of claim 1 which is: 5-(2-p-methyl-phenylpropyl)-2-{4-[4(2,3,4-trimethoxybenzyl)-piperazin-1-yl carbonyl]-3,3-dimethylbutyl}-thiophene.

6. A compound of claim 1 which is: 5-[3-(2,4-dimethylphenyl)-propyl]-2-{4-[4(2,3,4-trimethoxybenzyl)-piperazin-1-yl carbonyl]-3-methylbutyl}-thiophene.

7. A compound of claim 1 which is: 5-[3-(2,4-dimethylphenyl)-propyl]-2-{4-[4(2,3,4-trimethoxybenzyl)-benzyl)-piperazin-1-yl carbonyl]-3-dimethylbutyl}-thiophene.

8. A compound of claim 1 which is: 5-(4-p-methyl-phenybutyl)-2-{4-[4(2,3,4-trimethoxybenzyl)-piperazin-1-yl carbonyl]-3,3-dimethylbutyl}-thiophene.

* * * * *

UNITED STATES PATENT AND TRADEMARK OFFICE
CERTIFICATE OF CORRECTION

PATENT NO. : 5,175,294

DATED : Dec. 29, 1992

INVENTOR(S) : Michel Wierzbicki, Frédéric Sauveur, Jacqueline Bonnet, Martine Brisset, Charles Tordjman It is certified that error appears in the above-identified patent and that said Letters Patent is hereby corrected as shown below:

Title Page, [56] FOREIGN PATENT DOCUMENTS, Assistant Examiner; "F. Bernhardt" should read -- E. Bernhardt --.

Column 1, approximately line 44; "the" should read --they--.

Column 5, line 10; X,N," should read -- X,n, --.

Column 8, approximately line 46; "phenylpropionyl" should read -- phenylpropyl --.

Column 9, Table 3, continued, in the Table, Columns $R_1$ and $R_2$ together, line 10; insert an inverted horizontal bracket, as shown;

" 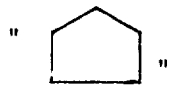 " should read 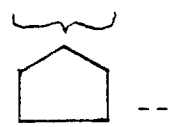 --

Column 9, 3rd line under the end of "TABLE 3, Continued"; "(3-phenylpropionyl)" should read -- (3-phenylpropyl) --.

Column 10, 2nd and 3rd line; "(3-phenylpropionyl)" should read --(3-phenylpropyl) --.

Column 10, 3rd line; "3,dimethylbutaryl)" should read --"3,dimethylbutyl) --.

Column 10, TABLE 4, Columns "$R_1$ and $R_2$ together, line 10;

"  " should read 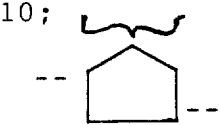 --

Column 11, approximately line 44; "After The" should read -- After the --.

Column 11, approximately line 44; "medium" should read --mixture--.

Column 12, last line; "with," should read -- which, --.

Column 16, approximately line 27; "-(2-" should read -- -2- --.

UNITED STATES PATENT AND TRADEMARK OFFICE
CERTIFICATE OF CORRECTION

PATENT NO. : 5,175,294

DATED : Dec. 29, 1992

INVENTOR(S) : Michel Wierzbicki, Frédéric Sauveur, Jacqueline Bonnet, Martine Brisset, Charles Tordjman It is certified that error appears in the above-identified patent and that said Letters Patent is hereby corrected as shown below:

Column 16, line 28; "-thiophene." should read -- -thiophene (alternate name: 5-(3-phenylpropyl)-2-(4-N-morpholino-carbonyl-3,3-dimethylbutyl)-thiophene).

Column 19, TABLE 10-continued, in the table columns $R_1$ and $R_2$ together, line "H" under Column "Xn":

"  " should read --  --

Column 25, line 1; Before the paragraph beginning "Refluxing", insert --18 g (0.045 mol) of 5-(3-phenylpropyl)-2(3,3-dimethyl-4-N-morpholinocarbonylbutyl)-thiophene(alternate name: 5-(3-phenylpropyl))-2(4-N-morpholinocarbonyl-3,3-dimethyl-butyl)-thiophene dissolved in 150 ml of ether are poured, drop by drop, into a suspension of 4 g (0.1 mol) of lithium aluminum hydride in 200 ml of ether at reflux.

Refluxing --.

Column 25, line 5; "distilled should read -- filtered --.
Column 25, line 6; "washed with 3 times" should read -- washed 3 times with --.
Column 26, line 5; "-(2-(3," should read -- -2-(3, --.
Column 28, TABLE 11-continued, heading of last column; "M.p. °C." should read -- M.p. °C (Kofler) --.
Column 30, TABLE 11-continued, heading of last column; "M.p. °C." should read -- M.p. °C. (Kofler) --.

UNITED STATES PATENT AND TRADEMARK OFFICE
CERTIFICATE OF CORRECTION

PATENT NO. : 5,175,294

DATED : Dec. 29, 1992

INVENTOR(S) : Michel Wierzbicki, Frédéric Sauveur, Jacqueline Bonnet, Martine Brisset, Charles Tordjman It is certified that error appears in the above-identified patent and that said Letters Patent is hereby corrected as shown below:

Column 32, TABLE 11-continued; heading of last column; "M.p. °C." should read --M.p. °C. (capillary tube) --.

Column 32, Example No. 49, 9th column; insert a ditto mark --"-- under the morpholino (structural formula).

Signed and Sealed this

Twenty-eighth Day of December, 1993

*Attest:*

BRUCE LEHMAN

*Attesting Officer*   *Commissioner of Patents and Trademarks*